United States Patent [19]

Taylor

[11] Patent Number: 5,578,047
[45] Date of Patent: Nov. 26, 1996

[54] HEMORRHOID REMOVING DEVICE

[76] Inventor: Jerry W. Taylor, 1825 King Rd., Mechanicsville, Md. 20659

[21] Appl. No.: 291,536

[22] Filed: Aug. 16, 1994

[51] Int. Cl.$^6$ .................................................. A61B 17/08
[52] U.S. Cl. .......................................... 606/157; 606/151
[58] Field of Search ................................. 277/215, 227; 606/1, 110, 112, 113, 135, 109, 139–141, 151, 157, 191–197, 144; 24/90 TA

[56] References Cited

U.S. PATENT DOCUMENTS

| | | | |
|---|---|---|---|
| 680,121 | 8/1901 | Burns | 24/90 TA |
| 1,610,309 | 12/1926 | Niederer | 24/90 TA |
| 1,619,541 | 3/1927 | Rehor | 24/90 TA |
| 4,226,239 | 10/1980 | Polk et al. | 606/141 |
| 4,526,385 | 7/1985 | Wheeler | 277/215 |
| 5,053,040 | 10/1991 | Goldsmith | 606/109 |
| 5,203,863 | 4/1993 | Bidoia | 606/112 |
| 5,303,937 | 4/1994 | Muss et al. | 277/215 |

*Primary Examiner*—Gary Jackson
*Assistant Examiner*—Glenn Dawson

[57] ABSTRACT

A hemorrhoid ligature element including an elongated cylindrical elastic body having a central bore. The outside of the body and the inner surface of the bore may have circumferential grooves for gripping tissue. The length of the element is substantially longer than the radius making the element roll-resistant.

1 Claim, 1 Drawing Sheet

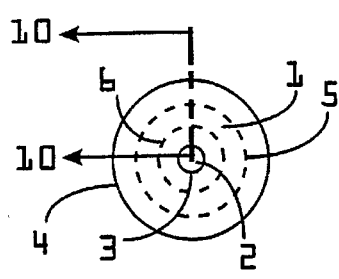
Fig. 1
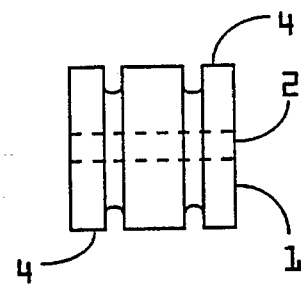
Fig. 2
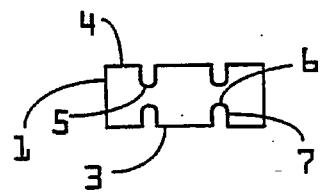
Fig. 3
Fig. 4A 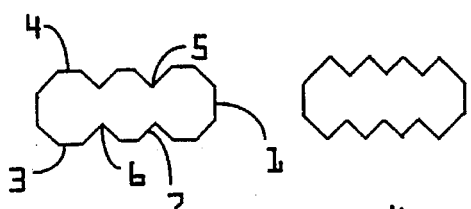 Fig. 4B
Fig. 4C 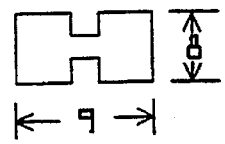 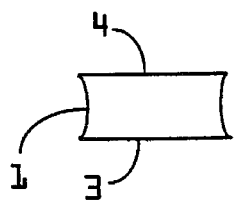 Fig. 4D

HEMORRHOID REMOVING DEVICE

The present invention relates to improvements in a ligature device used in removing hemorrhoids and the like from the colon by means of the so-called "throttling" surgery. The device, a ring like ligature element, is applied to the neck of the hemorrhoid until the hemorrhoid necrotizes and falls away due to the occlusion of blood supply pathways. The popularity of this type of surgery has increased in recent years because of its simplicity and cost savings.

Among the several objects of this invention is to increase the success rate for this common method of removing hemorrhoid and the like tissue from the colon. The increased success rate of this invention stems from improvements to its shape.

Unlike the design of the ligature already in use, this improved ligature element resists rolling or sliding away from the place where it is installed to remove hemorrhoid or the like tissue. Even when this invention is installed with the surface of the central opening accidentally reversed with the peripheral surface, it will perform the intended function, insuring that hemorrhoid or the like tissue is removed as planned, said improvements are beyond the abilities of the ligature element already in use which rolls or slides away from its installed location more easily.

With the foregoing and other objects which will be described or be apparent as the description proceeds, the invention consists of certain novel design of a ligature element device used in removing hemorrhoid and the like tissue from the colon. It is understood that the materials of construction and the shape of the invention may vary within the scope of its description without departing from the spirit of the invention as claimed.

BRIEF DESCRIPTION OF THE DRAWINGS

FIG. 1 shows the circular shape of the present invention with a central opening.

FIG. 2 shows the full width of the ligature element with circular grooves.

FIG. 3 is a sectional view taken on line 10—10, of FIG. 1.

FIG. 4 is a representative sampling of potential sectional views of the invention, all of which are from an equivalent viewpoint as line 10—10 of FIG. 1.

In these drawings, like numerals indicate like parts throughout all views and the number eight (8) refers to the depth of the ligature from opening surface to periphery surface and the number nine (9) refer to the width from end to end of the opening.

Referring now in detail to the Figures in the drawings, the elastic ring like body 1 of the ligature element has an approximately cylindrical opening 2 through the center and an approximately cylindrical periphery 4, substantially parallel to the opening.

A sectional view 10—10 (FIG. 3) of this improved ligature has a shape such as, but not limited to those shapes in FIG. 3 and FIG. 4.

In carrying out the intent of the present invention, the element is placed on a tool commonly used to install this type of ligature element, whereupon said tool stretches the element body 1 until the central opening 2 is large enough to receive the hemorrhoid or the like tissue to be removed, all tissue to be removed is then put through the enlarged opening 2 at which location the ligature element is set in place to remove said tissue by allowing the ligature to contract until the surface of the opening 3 joins the tissue, at such time said installing tool is withdrawn leaving the element installed at said set place, until the hemorrhoid or the like tissue is removed. When the ligature element is installed at the desired place, the near rectangular cross-sectional roll resistant shape of the body 1 (e.g. FIG. 3), inhibits the ligature element rolling across tissue put through the element's opening 2, wherein tissue returning through the opening because of said rolling is not removed. FIG. 3 and FIG. 4 show the improved shape being wider 9 than its depth 8, to inhibit the element rolling by means of the near rectangular shape, the rectangular characteristic causing it to remain at said installed place when subjected to naturally occurring pressures in the colon that would otherwise cause the element to roll away from its installed place.

After the element is set in place to remove hemorrhoid and the like tissue as described, the opening surface is pressed against tissue by the contracting force of the elastic ligature body, forcing the tissue it surrounds into the circular grooves 6 causing the sides of the grooves 7 to press against tissue, thereby increasing the coefficient of friction between the element and the tissue, wherein said friction inhibits incidental sliding of the element from said set place, thereby decreasing the ability of the element to slide and increasing the success rate of removing all tissue intended for removal.

Another improvement of the present invention is a slide resistant periphery surface 4, having grooves 5 shaped similar to the grooves 6 in the opening surface 3, which periphery surface if accidentally turned during installation to face the opening 2 would also inhibit the element sliding from the place where it is set to remove tissue; This improvement inhibits the element from sliding back across tissue put through the central opening, when installed with its periphery surface accidentally reversed with the opening surface.

What I claim and desire to be protected by this patent is:

1. A hemorrhoid ligature element comprising: an elongated, cylindrical elastic body having a central bore extending therethrough; the length of said body being substantially longer than a radius of said body measured from a periphery of said bore to an outer peripheral surface of said body, whereby said ligature element is roll-resistant; said outer peripheral surface including at least one circumferential groove for making the outer peripheral surface slide-resistant; said central bore including at least one circumferential groove extending radially into the body for receiving tissue therein, thereby increasing a coefficient of friction between the ligature element and the tissue.

* * * * *